United States Patent [19]

Toyoda et al.

[11] Patent Number: 4,988,586

[45] Date of Patent: Jan. 29, 1991

[54] METHOD FOR THE PREVENTION OF FUSARIUM DISEASES AND MICROORGANISMS USED FOR THE SAME

[75] Inventors: Hideyoshi Toyoda, Hirakata; Ryutaro Utsumi, Nara, all of Japan

[73] Assignee: Daikin Industries, Ltd., Osaka, Japan

[21] Appl. No.: 72,130

[22] Filed: Jul. 10, 1987

[30] Foreign Application Priority Data

| Jul. 11, 1986 | [JP] | Japan | 61-164335 |
| Feb. 13, 1987 | [JP] | Japan | 62-32269 |
| Feb. 13, 1987 | [JP] | Japan | 62-32270 |
| Feb. 13, 1987 | [JP] | Japan | 62-32271 |

[51] Int. Cl.$^5$ .................. A61K 37/00; C12N 15/00; C12N 1/20; C12N 1/12
[52] U.S. Cl. .................. 424/93; 435/172.1; 435/172.3; 435/874; 435/849; 435/822; 435/252.33; 435/253.3; 435/252.31; 435/252.1

[58] Field of Search .............. 435/170, 171, 172.3, 435/253, 254, 874, 929, 172.1, 252.33, 253.3, 252.31, 252.1; 514/345, 392; 424/93

[56] References Cited

U.S. PATENT DOCUMENTS

| 4,479,936 | 10/1984 | Vandenbergh et al. | 424/93 |
| 4,595,589 | 6/1986 | Tahvonen | 424/93 |
| 4,714,614 | 12/1987 | Scher | 424/93 |
| 4,748,021 | 5/1988 | Chet et al. | 424/93 |
| 4,798,723 | 1/1989 | Dart et al. | 424/93 |

*Primary Examiner*—Robin L. Teskin
*Attorney, Agent, or Firm*—Irell & Manella

[57] ABSTRACT

A method for the prevention of Fusarium diseases comprising the application of a microorganism that decomposes or detoxifies fusaric acid to the plant or to the soil. The microorganisms are the genuses Cladosporium and Pseudomonas that have the ability to decompose and/or detoxify fusaric acid.

6 Claims, 1 Drawing Sheet

METHOD FOR THE PREVENTION OF FUSARIUM DISEASES AND MICROORGANISMS USED FOR THE SAME

BACKGROUND OF THE INVENTION

1. Field of the Invention

This invention relates to a method for the prevention of Fusarium disease by the use of microorganisms that have the ability to decompose or detoxify fusaric acid.

2. Description of the Prior Art

It is known that the genus Fusarium contains species that can cause diseases of wither and blight that occur during the growth of plants, such as vine-splitting of members of the gourd family such as cucumbers, watermelons, melons, etc., tomato blight, half-wither disease of eggplants, yellow blight of strawberries, dry rot of devil's foot root, spring blight of grass, etc., by infecting the plants. These kinds of infectious diseases are caused by species of Fusarium named *Fusarium oxysporum*, *Fusarium moniliform*, and a large number of other species. These fungi contaminate the soil, and are absorbed into the plant from the soil via the xylem. It is thought that the cause of the withering of plants is the fusaric acid that is produced by the metabolism of these fungi. Fusaric acid is produced by almost all species that belong to the genus Fusarium (including the two species mentioned above) that are plant pathogens. This fusaric acid acts as a non-specific toxin, and it damages not only the host plants but also other kinds of plants. Fusaric acid causes an increase in the permeability of plant protoplasmic membranes with respect to tissue fluids that contain $Ca^{2+}$, $K^+$, $Na^+$, or other cations, or that contain various kinds of amino acids, which increase causes exudation of the tissue fluids to surfaces such as those of the leaves of the plant. This exudate dries, and the surfaces of the plants develop high osmotic pressure, which increases the evaporation of water still more. As a result, the plant dies of wilting.

Chemical agents that are used to prevent Fusarium infections include, for example, the o-phenylenediamine derivative with the structure shown below, with the trade name of Topjin-M, which is used as a soil fungicide.

This agent kills the fungi of the genus Fusarium that live in the soil, but if it merely scattered on the surface of the soil, it is not effective, so it is necessary to mix it into the soil before sowing or planting. This operation requires much labor. There is also the disadvantage that once the symptoms of the infection have appeared, this agent has almost no effect on stopping the progress of the disorder.

There is a variety of tomato that is resistant to infections caused by species of Fusarium. It has been found that, in the tissues of this variety of tomato, as shown below, fusaric acid (I) is metabolized and decomposed to form N-methylfusaric acid amide (II). The decomposition of fusaric acid is attained effectively among varieties of tomatoes that have strong resistance to Fusarium infections.

If fusaric acid is made nontoxic in this way by decomposition or chemical modification, it might be possible to prevent plants from losing water, which damages the metabolism of water components. For example, if a microorganism was found that decomposed or detoxified fusaric acid, it could be used as an effective method for the prevention of Fusarium diseases. In addition, if the gene that controls the decomposition or detoxification of fusaric acid could be isolated, it might be possible to obtain microorganisms potent in the causing of this effect, and these microorganisms would be useful in the prevention of such plant diseases.

SUMMARY OF THE INVENTION

The method for the prevention of Fusarium diseases of this invention, which overcomes the above-discussed and other numerous disadvantages and deficiencies of the prior art, comprises the application of a microorganism which decomposes or detoxifies fusaric acid to the plant or to the soil.

In a preferred embodiment, the microorganism is a wild-type microorganism, a mutant of the wild-type microorganism, or a transformant obtained by gene manipulation of the wild-type microorganism or the mutant.

In a preferred embodiment, the microorganism belongs to the genus Cladosporium. In a more preferred embodiment, the microorganism is *Cladosporium werneckii*. In a still more preferred embodiment, the microorganism is the strain *Cladosporium werneckii* DK2011 (FERM BP-1383).

In a preferred embodiment, the microorganism belongs to the genus Pseudomonas. In a more preferred embodiment, the microorganism is *Pseudomonas cepacia*. In a still more preferred embodiment, the microorganism is the strain *Pseudomonas cepacia* UK-1 (FERM BP-1385).

In a preferred embodiment, the microorganism is *Pseudomonas solanacearum* and is not pathogenic itself. In a more preferred embodiment, the microorganism is obtained by a treatment to cause mutation of the non-pathogenic *Pseudomonas solanacearum*. In a still more preferred embodiment, the microorganism is the strain *Pseudomonas solanacearum* N50A16 (FERM BP-1384).

In a preferred embodiment, the microorganism is *Escherichia coli* into which the gene controlling the decomposition or detoxification of fusaric acid from *Cladosporium werneckii* DK2011 has been introduced. In a more preferred embodiment, the *E. coli* is the strain pFS4/HB101 (FERM BP-1386).

A microorganism of this invention belongs to the genus Cladosporium and has the ability to decompose fusaric acid.

In a preferred embodiment, the microorganism is *Cladosporium werneckii*. In a more preferred embodiment, the microorganism is the strain *Cladosporium werneckii* DK2011 (FERM BP-1383).

Another microorganism of this invention belongs to the genus Pseudomonas and has the ability to decompose fusaric acid.

In a preferred embodiment, the microorganism is *Pseudomonas cepacia*. In a more preferred embodiment, the microorganism is the strain *Pseudomonas cepacia* UK-1 (FERM BP-1385).

Another microorganism of this invention belongs to the species *Pseudomonas solanacearum*, being not pathogenic itself, and has the ability to detoxify fusaric acid for plants. In a preferred embodiment, the microorganism is obtained by a treatment to cause mutation of *Pseudomonas solanacearum*. In a more preferred embodiment, the microorganism is the strain *Pseudomonas solanacearum* N50A16 (FERM BP-1384).

A gene of this invention controls the decomposition or detoxification of fusaric acid which is derived from the above-mentioned microorganisms.

Thus, the invention described herein makes possible the objects of (1) providing a wild-type microorganism that has the ability to decompose or detoxify fusaric acid; (2) providing a mutant of the wild-type microorganism that has the ability to decompose or detoxify fusaric acid; (3) providing a gene from the above-mentioned microorganisms that can decompose or detoxify fusaric acid; (4) providing a transformant into which said gene has been introduced, thereby causing the decomposition or detoxification of fusaric acid; (5) providing a method for the prevention of Fusarium diseases such as vine splitting and blight caused by members of the genus Fusarium by the use of at least one of the microorganisms mentioned above as having the ability to decompose or detoxify fusaric acid.

BRIEF DESCRIPTION OF THE DRAWING

This invention may be better understood and its numerous objects and advantages will become apparent to those skilled in the art by reference to the accompanying drawing as follows.

DESCRIPTION OF THE PREFERRED EMBODIMENTS

In this invention, "microorganisms that have the ability to decompose or to detoxify fusaric acid" is taken to mean those by which fusaric acid is decomposed or chemically modified so as to make said fusaric acid non-toxic to plants. Such microorganisms can be isolated from wild-type microorganisms, and also can be obtained by the mutation of the wild-type microorganisms or by gene manipulation of the wild-type microorganisms and/or the mutant.

The above-mentioned microorganisms that have the ability to decompose fusaric acid can be grown on medium with fusaric acid as the sole carbon source and/or as the sole nitrogen source, so screening can be done, for example, with culture medium 1 with fusaric acid as the sole carbon source or culture medium 2 with fusaric acid as the sole nitrogen source, as follows:

| Culture Medium 1: | |
|---|---|
| $K_2HPO_4$ | 7 g |
| $KH_2PO_4$ | 2 g |
| $MgSO_4$ | 0.1 g |
| $(NH_4)_2SO_4$ | 1 g |
| Fusaric acid | 100 mg |
| Water | 1 l |

| Culture Medium 2: | |
|---|---|
| Glucose | 2 g |
| $NaH_2PO_4\ H_2O$ | 0.5 g |
| $K_2HPO_4$ | 0.5 g |
| $MgSO_4\ 7H_2O$ | 0.2 g |
| $CaCl_2$ | 0.1 g |
| Fusaric acid | 100 mg |
| Water | 1 l |

Moreover, microorganisms that have the ability to detoxify fusaric acid chemically have resistance to fusaric acid and also have the ability to detoxify the fusaric acid for plants. Selection of these microorganisms can be made as follows: For example, screening is carried out with culture media 3 or 4 mentioned below that have fusaric acid at the concentration of 100 μg/ml, and then, by the use of the culture fluid of the medium that contains fusaric acid, a check is made to see if the fluid is toxic for plants. To check whether or not the culture fluid is toxic to plants, checking can be done with, for example, tomato callus or tomato cuttings (see Examples).

| Culture Medium 3: | |
|---|---|
| Peptone | 10 g |
| Casamino acid | 1 g |
| Glucose | 10 g |
| Fusaric acid | 100 mg |
| Water | 1 l |
| pH | 6.5 |

| Culture Medium 4: | |
|---|---|
| $NH_4Cl$ | 1 g |
| $Na_2HPO_4$ | 7 g |
| $KH_2PO_4$ | 3 g |
| NaCl | 0.5 g |
| $CaCl_2$ | 0.1 g |
| $MgSO_4$ | 1 g |
| Casamino acid | 4 g |
| Fusaric acid | 100 mg |
| Water | 1 l |
| pH | 6.5 |

For example, wild-type microorganisms are screened with the culture media listed above, and the culture fluid is used as needed to check whether it is nontoxic for plants, resulting in the finding of microorganisms that can decompose or detoxify fusaric acid. As such wild-type microorganisms, for example, members of the genus Cladosporium and members of the genus Pseudomonas can be mentioned. Of the members of the genus Cladosporium, the species *Cladosporium werneckii*, and especially the strain *Cladosporium werneckii* DK2011 (FERM BP-1383), are particularly suitable. Of the members of the genus Pseudomonas, the genus *Pseudomonas cepacia* and especially the strain *Pseudomonas*

*cepacia* UK-1 (FERM BP-1385) are particularly suitable.

As mutant strains of the wild-type microorganisms, for example, non-pathogenic strains of the species *Pseudomonas solanacearum* can be mentioned. In general, members of the species *Pseudomonas solanacearum* are known as the pathogens in bacterial wilt disease of members of the eggplant family and in damping-off of tobacco. However, non-pathogenic strains are also known. The original strain that is non-pathogenic is treated by ordinary methods for the causing of mutation, resulting in mutants, some of which can decompose or detoxify fusaric acid. These mutants are selected by the ordinary processes. As methods for causing mutation, the N-methyl-N'-nitro-N-nitrosoguanidine (NTG) method of Adelberg et al. (*Biochem. Biophys. Res. Comm.*, 18, 788 (1965), X-ray radiation, UV irradiation, etc., can be used. For mutants to be obtained in this way, the *Pseudomonas solanacearum* strain N50A16 (FERM BP-1384) that detoxifies fusaric acid is preferable. This strain N50A16 was obtained by the mutation treatment of the non-pathogenic strain *Pseudomonas solanacearum* TU-10A.

To obtain microorganisms that are produced by gene manipulation of the wild-type microorganisms and that decompose or detoxify fusaric acid, first, DNA is isolated from the microorganism mentioned above that can decompose or detoxify fusaric acid, by the ordinary methods. The gene that is concerned in the above-mentioned ability to decompose or detoxify fusaric acid is cloned, and introduced into another microorganism, resulting in a transformant that can decompose or detoxify fusaric acid. As the host microorganism, for example, *E. coli* can be mentioned. In addition, microorganisms that grow inside plants, preferably, within the xylem, and/or that are competitive with Fusarium fungi are suitable for use. As a microorganism that grows in the xylem of plants, there are the non-pathogenic strains of *Pseudomonas solanacearum*, etc. As microorganisms that grow in competition with Fusarium species, there are the following: members of the genus Streptomyces (preferably, Streptomyces sp. ATCC 39434), species of the genus Serratia (preferably *Serratia marcescens*), members of the genus Pseudomonas (preferably *Pseudomonas fluorescens*, *Pseudomonas putida*, or *Pseudomonas cepacia*), and members of the genus Bacillus (e.g., *Bacillus subtilis*). As transformants with the ability to decompose or detoxify fusaric acid that are obtained by gene manipulation, for example, *E. coli* strain pFS4/HB101 (FERM BP-1386), into which the gene that is concerned with the decomposition or detoxification of fusaric acid from the strain *Cladosporium werneckii* DK 2011 mentioned above has been introduced, is preferable.

The bacteriological characteristics, identification, culture conditions, etc., of the microorganisms representative of those that can decompose or detoxify fusaric acid, *Cladosporium werneckii* DK 2011, *Pseudomonas cepacia* UK-1, *Pseudomonas solanacearum* N50A16, and *Escherichia coli* pFS4/HE101, are as shown below.

(1) *Cladosporium werneckii* DK 2011

This stain was isolated by the inventors of this invention from soil.

(1)-1 Bacteriological characteristics and species identification

This is a strain of Fungi imperfecti with blastospores that form mainly yeast-like colonies and with hyphae that form mainly villous-like colonies. The blastoconidia are 2–4×4–8 μm. The hyphae have septa, and are 2.9–5.8 μm width. From these morphological characteristics and growth habit, by reference to the Illustrated Manual of Fungi (S. Udagawa et al., Kodansha Scientific, Japan, 1978; p. 863), this species was identified as a strain of *Cladosporium werneckii*. The inventors of this invention named the strain *Cladosporium werneckii* DK 2011 (FERM BP-1383).

(1)-2 Culture conditions

Special culture medium is not required. To the minimal medium that contains phosphates, sulfate, chloride, etc., with potassium, sodium, magnesium, etc., fusaric acid and sugars can be added as carbon sources. To enhance the ability of this microorganism to decompose fusaric acid, it is preferable to have fusaric acid in the medium as the carbon source. As the nitrogen source to be used in this minimal medium, besides fusaric acid, inorganic nitrogen such as nitrate, ammonium salt, etc., and organic nitrogen with amino groups can be used. As the source of nutrients, it is possible to add corn steep liquor, yeast extract, etc., as needed. The temperature of culture can be in the range of 15° to 35° C., and preferably around 25° C. The culture pH can be in the range of 6 to 9, and preferably around 7. Culture is for from 3 days to one week aerobically with agitation or oscillation. Solid culture (on an agar medium) is possible.

(1)-3 Decomposition of fusaric acid

When this microorganism is cultured as described above, and when the cells obtained are then cultured with aeration in an ordinary medium that contains fusaric acid, with the concentration of fusaric acid in the medium at 50–200 ppm (μg/ml), almost all of the fusaric acid is decomposed. Moreover, when this microorganism is grown in advance in a suitable medium, the resting cells, a cell homogenate, or a cell extract can be used to cause the decomposition of fusaric acid. For example, almost all of the fusaric acid in the model reaction system described below was decomposed.

| Composition |
|---|
| Phosphate buffer (pH 7.0) |
| Fusaric acid |
| Water |
| Cells, cell homogenate, or cell extract |

The amount of cells, cell homogenate, or cell extract to be used in the model reaction system described above is 1–10% by weight (wet weight) of the reaction system, and preferably 4–6% by weight (wet weight). The cell homogenate can be obtained by the use of an ultrasonic oscillator or a French press. The cell extract can be obtained by centrifugal separation of a cell homogenate. The pH of the reaction mixture should be in the range of 6 to 9. It is preferable to adjust the pH to around 7. The concentration of fusaric acid should be 20–200 ppm, and preferably in the range of 50 to 100 ppm. As buffer, a 50 mM phosphate buffer can be used, but the buffer is not limited thereto. The reaction temperature should be in the range of 10° to 35° C. Preferably, it should be around 30° C. When resting cells are used, without marked proliferation of the cells, almost all of the fusaric acid can be decomposed.

The amount of fusaric acid in the above system can be calculated from measurements of the optical absorbance ($OD_{270}$).

(2) Pseudomonas cepacia UK-1

This strain was isolated from soil by the inventors of this invention.

(2)-1 Bacteriological characteristics and species identification

The bacteriological characteristics are shown in Table 1.

TABLE 1

| Bacteriological characteristics | | |
|---|---|---|
| (a) Morphology | | |
| ① | Shape and size of cells | Short rods (0.75 – 1.0) × (1.4 – 2.4) μm |
| ② | Mobility | Present |
| | Flagellation | Several polar flagella |
| ③ | Gram staining | Negative |
| (b) Growth on different media | | |
| ① | King A medium | Yellowish-brown colonies formed with rough surfaces. |
| ② | King B medium | Yellowish-white colonies formed. |
| ③ | Pseudomonas F medium | Colonies colored white with a yellowish-green tinge formed. |
| ④ | Pseudomonas P medium | Dark greenish-brown colonies with edges colored white with a yellowish-green tinge formed. |
| ⑤ | MYP (mannitol:yeast extract:peptone) medium | Yellowish-green colonies formed. |
| ⑥ | Litmus milk | Bleaching was seen. |
| (c) Physiological characteristics | | |
| ① | Reduction of nitrate | + |
| ② | Denitrification reaction | − |
| ③ | MR (Methyl Red) test | − |
| ④ | VP (Voges-Proskauer) test | − |
| ⑤ | Indole production | − |
| ⑥ | Hydrogen sulfide production | |
| | (lead acetate test-paper method) | − |
| | (TSI (Triple-Sugar Iron) agar culture method) | − |
| ⑦ | Starch hydrolysis | − |
| ⑧ | Utilization of citric acid | |
| | Koser culture medium | + |
| | Christensen's culture medium | + |
| ⑨ | Utilization of inorganic nitrogen | |
| | Nitrate | + |
| | Ammonium salt | + |
| ⑩ | Production of pigments | |
| | King A medium | Yellowish-brown pigment was scattered in the medium. Fluorescent pigment was not produced. |
| | King B medium | Fluorescent pigment was not produced. |
| | Pseudmonas F medium | Fluorescent pigment was not produced. |
| | Pseudmonas P medium | A brown pigment with a yellowish-green tinge was found scattered in the medium. Fluorescent pigment was not produced. |
| | MYP (mannitol:yeast extract:peptone) medium | A yellowish-green pigment was found scattered in the medium. Fluorescent pigment was not produced. |
| ⑪ | Oxidase | + |
| ⑫ | Catalase | + |
| ⑬ | Growth limits ph | 4.0~9.0 |
| | Optimum pH | 5.5~6.5 |
| | Temperature | 10~40° C. |
| ⑭ | Oxygen requirements | Aerobic |
| ⑮ | O-F test (Hugh-Leifson method) | |
| | Glucose | (Acid was not produced) |
| | Galactose | (Acid was not produced) |
| | Lactose | (Acid was not produced) |
| ⑯ | Acid production from sugars | |
| | Glucose | + |
| | Galactose | + |
| | Lactose | ± |
| | Maltose | ± |
| ⑰ | Nutritional requirements | − |
| ⑱ | Nutritional characteristics Utilization of | |
| | Glucose | + |
| | Galactose | + |
| | Sucrose | + |
| | Rhamnose | − |
| | Maltose | − |
| | Lactose | − |
| | Ethanol | + (Weak) |
| | 2,3-Butanediol | + |
| | m-Hydroxybenzoic acid | + |
| | Putrescine | + |

TABLE 1-continued

| Bacteriological characteristics | | |
|---|---|---|
| | Heptanoic acid | + |
| | Inulin | − |
| | Acetic acid | + |
| | Adipic acid | + |
| | Adonitol | + |
| | Benzoic acid | + |
| | p-Hydroxybenzoic acid | + |
| | β-Hydroxybutyric acid | + |
| | Succinic acid | + |
| | Citric acid | + |
| (19) | Poly-β-hydroxybutyric acid (PHB) accumulation | + |
| (20) | Tween decomposition | |
| | Tween 40 | + |
| | Tween 60 | + |
| | Tween 80 | + |
| (21) | Gelatin liquefaction | + |
| (22) | 3-Ketolactose production | − |
| (23) | Arginine dehydrolase | − |
| (24) | Dioxyacetone production | − |
| (25) | Extracellular DNase | − |
| (26) | Ability to oxidize gluconic acid | − |
| (27) | Decomposition of protocatechuic acid | Cleavage at ortho position |

This fungus was identified by reference to Bergey's Manual of Systematic Bacteriology, Volume 1, 1984 as a strain of *Pseudomonas cepacia* by its bacteriological characteristics listed above. This strain was named *Pseudomonas cepacia* UK-1 (FERM BP-1385) by the inventors of this invention.

(2)-2 Culture conditions

The same medium as for (1)-2, *Cladosporium werneckii* DK 2011, can be used. The culture temperature is 15°-40° C., and preferably 25°-30° C. The pH of the medium should be 4.0-9.0, and preferably 5.5-6.5. Culture is for one to five days aerobically, with agitation or oscillation. It is also possible for solid medium (agar medium) to be used.

(2)-3 Decomposition of fusaric acid

When this microorganism is grown under the culture conditions described above, then when it is grown aerobically in an ordinary medium that contains fusaric acid, the fusaric acid in the medium is almost completely decomposed.

In the same way as for the *Cladosporium werneckii* DK 2011 mentioned above, it is possible to decompose fusaric acid by the use of resting cells, a cell homogenate, or a cell extract. For example, in the model reaction system of the following table, the fusaric acid can be almost completely decomposed.

| Composition |
|---|
| Physiological saline, phosphate buffer, etc. |
| Fusaric acid |
| Cells, cell homogenate, or cell extract |

Cells, cell homogenate, and cell extract are obtained in the same way as for the strain DK2011 described above, and the volume used is also about the same. The reaction should be within the pH range of 4-9, and preferably, it is adjusted to within the range of pH 5-7. The concentration of fusaric acid should be 2000 ppm or less, and preferably from 50 to 300 ppm. As the buffer mentioned above, for example, a 50 mM buffer can be used. The reaction temperature should be within the range of 15°-40° C., and preferably from 25° to 30° C. When resting cells are used, without marked growth of the cells, almost all of the fusaric acid can be decomposed. The reaction time depends on the cell concentration, fusaric acid concentration, temperature, pH, etc., but generally, it should be from several minutes to 72 hours.

(2)-4 Other characteristics of *Pseudomonas cepacia* UK-1

This strain has, in addition to the ability to decompose fusaric acid, which has been described above, the ability to inhibit the growth of plant pathogens. This strain of bacteria was grown on different kinds of media with various plant pathogens, and the extent of its inhibition of the growth of the pathogens was rated on a six-point scale (−, ±, +, ++, +++, ++++). The media, pathogens, and inhibition are shown in Table 2. The media used were Zapek-Dox medium (ZD), Zapek medium (Z), potato glucose agar (PGA), and potato sucrose agar (PSA); plate culture was used. The pathogens were inoculated into the center of the medium, and the UK-1 strain was inoculated into the medium in four locations around the center at equal intervals. The evaluation was as follows: The symbol ++++ was used to mean that the pathogen grew over the entire surface of the medium, and that its growth was not inhibited at all. The symbol ± meant that there was some slight inhibition. The symbol was used to mean that inhibition of the growth of the pathogen was complete.

TABLE 2

| | Medium | | | | Disease caused by |
|---|---|---|---|---|---|
| Plant pathogen | ZD | Z | PDA | PSA | pathogen |
| *Fusarium oxysporum* f. sp. *lycopersici* race J1 | ++ | ++ | +++ | ++++ | Tomato blight |
| *Fusarium oxysporum* f. sp. *lycopersici* race J3 | ++ | ++ | +++ | ++++ | Tomato blight |
| *Fusarium oxysporum* f. sp. *lagenariae* | ++ | +++ | +++ | ++++ | Bottle gourd vine-splitting |
| *Fusarium oxysporum* f. sp. *melonis* | ++++ | +++ | +++ | ++++ | Melon vine-splitting |
| *Mycosphaerella melonis* | +++ | +++ | +++ | ++++ | Melon vine-splitting |
| *Alternaria alternata* tomato | | | | | Tomato stem blight |

(3) Pseudomonas solanacearum N50A16

This strain was obtained by treatment to cause mutation of the non-pathogenic strain *Pseudomonas solanacearum* TU-10A by the method of Adelberg et al. (Biochem. Biophys. Res. Comm., 18, 788 (1965)) using N-methyl-N'-nitro-N-nitrosoguanidine (NTG).

(3)-1 Method for the isolation of *Pseudomonas solanacearum* N50A16

*Pseudomonas solanacearum* is generally known as the pathogen in bacterial wilt disease in members of the eggplant family and in damping-off of tobacco. However, there are strains of *Pseudomonas solanacearum* that have no pathogenicity. It is easy to distinguish between the pathogenic and non-pathogenic strains of *Pseudomonas solanacearum*. For example, when strains of *Pseudomonas solanacearum* isolated from soil are cultured on a PCG medium (containing 1% peptone, 0.1% casamino acids, and 1% glucose at pH 6.5) that includes 0.005% tetrazolium chloride, the pathogenic strains form fluid colonies that are irregular in shape. These colonies are first white, and then take on a reddish tinge. The non-pathogenic strains form reddish-brown circular colonies with a diameter of 2 to 3 mm. When non-pathogenic strains are cultured repeatedly, reversion to the pathogenic is uncommon. To check for the presence of pathogenicity in a strain of *Pseudomonas solanacearum*, one way is to use the root-opening contact method (see Examples) with tobacco plants or tomato plants about 1 month after sprouting. When the strain is non-pathogenic, the plants mentioned above will show no pathological changes, but when a pathogenic strain is used, the plants will die of wilt in 7 to 10 days.

The strain Pseudomonas solanacearum N50A16 was obtained by the treatment to cause mutation of a non-pathogenic strain of *Pseudomonas solanacearum* like those mentioned above. Treatment for mutation was by the method of Adelberg et al. with the use of N-methyl-N'-nitro-N-nitrosoguanidine (NTG). Colonies on the medium were used for inoculation of a PCG medium that contained 100 ppm of fusaric acid. The growth of the said parent strain, the non-pathogenic strain of *Pseudomonas solanacearum*, is completely inhibited by the presence of 100 ppm of fusaric acid, but the mutated non-pathogenic strain of *Pseudomonas solanacearum* can grow on medium that contains this amount of fusaric acid. Then, from the strains that grow on the above-mentioned medium, strains that have the ability to detoxify fusaric acid for plants are screened using tomato callus, etc. The strains obtained in this way are new strains of *Pseudomonas solanacearum* that have the ability to detoxify fusaric acid. From the strains that were obtained, the strain that had the strongest ability to detoxify fusaric acid was selected, and this was named *Pseudomonas solanacearum* N50A16 by the inventors of this invention.

(3)-2 Bacteriological characteristics

The bacteriological characteristics are shown in the following Table 3.

TABLE 3

| Bacteriological characteristics | | |
|---|---|---|
| (a) Morphology | | |
| (1) Shape and size of cells | Rods | |
| | (0.5 − 0.7) × | |
| | (1.5 − 2.5) μm | |
| (2) Gram staining | Negative | |
| (3) Mobility | Presence | |
| Flagellation | Several polar flagella | |
| (b) Physiological characteristics | | |
| (1) Reduction of nitrate | Positive | |
| (2) Oxygen requirements | Aerobic | |
| (3) Catalase | Positive | |
| (4) Oxidase | Positive | |
| (5) Growth limits | No growth at 41° C. or more | |
| (6) Gelatin liquefaction | Negative | |
| (7) Starch hydrolysis | Negative | |
| (8) Other characteristics | Accumulates poly-β-hydroxybutyric acid | |
| (9) Nutritional characteristics Utilization of | | |
| D-Glucose | + | |
| Acetic acid | + | |
| Propionic acid | + | |
| Butyric acid | + | |
| Isobutyric acid | + | |
| Succinic acid | + | |
| Fumaric acid | + | |
| L-malic acid | + | |
| Citric acid | + | |
| Pyruvic acid | + | |
| Glycerine | + | |
| Sucrose | + | |
| Benzoic acid | + | |
| Trehalose | + | |
| Asparagine | + | |
| L-Histidine | + | |
| D-Xylole | − | |
| L-Arabinose | − | |
| Glycine | − | |
| L-Valine | − | |
| L-Tryoptophan | − | |
| n-Propanol | − | |
| n-Butanol | − | |
| Malonic acid | − | |
| Maleic acid | − | |
| Inulin | − | |

(3)-3 Culture conditions

Special medium is not needed. To a minimal medium that contains phosphate, sulfate, chloride, etc., with potassium, sodium, magnesium, etc., fusaric acid, sugars such as glucose, sucrose, etc., casamino acid, etc., can be added as the carbon source. As the nitrogen source to be used in this minimal medium, inorganic nitrogen such as nitrate, ammonium salt, and/or organic nitrogen with amino groups can be added. As the source nutrients, it is possible to add corn steep liquor, yeast extract, etc., as needed. The temperature of culture can be 10°–40° C., and preferably around 26° C. The culture pH can be 4–8, and preferably around 6.5. Culture should be from 3 to 7 days aerobically, with agitation or oscillation. Solid culture (agar medium) is also possible.

(3)-4 Detoxification of fusaric acid

When this microorganism is grown in culture as described above, the obtained cells and/or culture fluid when brought into contact with fusaric acid detoxifies the fusaric acid so that it is no longer toxic for plants (here both loss of toxicity and a decrease in toxicity is meant). The mechanism by which this kind of microorganism detoxifies fusaric acid is thought to involve the decomposition of fusaric acid, its chemical modification, or both.

(4) *Escherichia coli* pFS4/HB101

This strain was obtained by the introduction, into the chromosome of *E. coli* HB101, of the gene from *Cladosporium werneckii* DK 2011 that controls the decomposition or detoxification of fusaric acid.

(4)-1 Preparation of *E. coli* pFS4/HB101

Cells of *Cladosporium werneckii* DK 2011 were disrupted, and the method of Johnston et al. (EMBO Journal 4, 1307-1311 (1985)) was used to cleave the DNA so as to obtain a number of DNA fragments. These fragments were cloned into a vector pNO1523, resulting in a DNA library, which was then transfected into the host, *Escherichia coli* HB101, which has been treated with $CaCl_2$ so as to permit foreign DNA to enter thereinto. The recombinants obtained can be screened, for example, on the medium containing fusaric acid described above, for selection for resistance to fusaric acid. The bacteria resistant to fusaric acid are then cultured on a medium that contains fusaric acid, and the culture filtrate is tested for toxicity to plants, by which it is possible to find if there are any microorganisms that can decompose or detoxify fusaric acid among said microorganisms that are resistant to fusaric acid. From the recombinants obtained in this way that can decompose or detoxify fusaric acid, the plasmids are removed by the alkaline SDS method, etc., and cleaved with a variety of restriction enzymes. In this way it is possible to identify tentatively the position of the gene that controls the decomposition or detoxification of fusaric acid.

Figure 1:
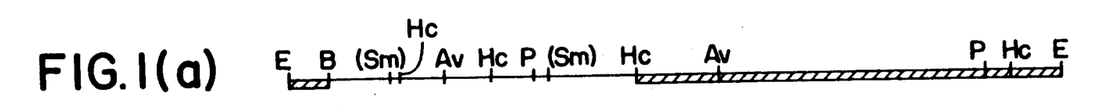
FIG. 1 is a restriction map of the gene obtained by this invention, which includes the plasmid pFS4.

By the above method, the above-mentioned DNA fragments were cloned into the SmaI site of pNO1523 to obtain plasmids (the SmaI position in the vector plasmid pNO1523 is lost; and the SmaI site lost is shown in FIG. 1 as Sm in parentheses), which are then transfected into the host cell, *E. coli* HB101, resulting in transformants. One of the transformants with the greatest ability to detoxify fusaric acid was selected and named pFS4/HB101.

This plasmid (pFS4) of the recombinant pFS4/HB101 was cleaved by a number of restriction enzymes, and the restriction map obtained are shown in FIGS. 1*a* to 1*e*. FIG. 1*a* shows plasmid pFS4. FIG. 1*a'* is an enlargement showing the foreign parts. The hatching shows the gene derived from the vector pBR322. FIGS. 1*b* to 1*e* show the DNA fragments cleaved by different restriction enzymes.

The host bacterium, *E. coli* HB101, is resistant to streptomycin, but when, for example, vector plasmid pNO1523 only is introduced thereinto, the gene that codes for streptomycin sensitivity from pNO1523 is now present in the said bacterium, and the dominant characteristic, sensitivity to streptomycin, is expressed. Plasmid pFS4 is constructed so that the above-mentioned plasmid pNO1523 is cleaved at the sole cleavage position for SmaI in the gene for streptomycin sensitivity and the foreign DNA is introduced into the cleaved portion, which inactivates the gene for streptomycin sensitivity. For that reason, the strain pFS4/HB101 becomes resistant to streptomycin. This plasmid pFS4 has a gene for ampicillin resistance at another location, so the strain pFS4/HB101 becomes resistant to both streptomycin and to ampicillin.

(4)-2 Bacteriological characteristics

This strain has, in addition to the characteristics of the host, the ability to detoxify fusaric acid.

(4)-3 Culture conditions

Culture is the same as for that of the host, *E. coli* HB101 as described by Ozeki and Shimura (Lectures in Genetic Experimentation Vol. 1 (1983) published by Kyoritsu Shuppan).

(4)-4 Detoxification of fusaric acid

When this strain is grown under the appropriate culture conditions, the cells obtained and/or their culture fluid detoxifies fusaric acid for plants when brought into contact with the fusaric acid. These kinds of microorganisms that have the ability to decompose or detoxify fusaric acid (for example, the above-mentioned (1)–(4)), when applied to plants or to the soil, can prevent plant diseases (Fusarium diseases) that involve fusaric acid. The methods for the application of these microorganisms are as follows: for example, (a) inoculation into the plant; (b) the method of coating of the seeds; and (c) the method of mixing with the soil. The methods (a) of inoculation into the plant include (a)-1, the method in which at least one portion of the root of the growing plant is excised with a razor blade, etc., and the microorganism mentioned above that can decompose or detoxify fusaric acid is applied (for example, a bacterial suspension is poured onto the plant roots excised with a razor blade), called the injured root inoculation method; (a)-2, the method in which a microsyringe and an injection device are used to inject a suspension of the microorganisms mentioned above into the base portion of the plant; (a)-3, the method in which a plant stalk is cut and the cut end is placed into a suspension of the microorganisms mentioned above and then dipped in water, until new advertitious roots grow; and (a)-4, the method in which the plant is sprayed under pressure with a suspension of the microorganism mentioned above containing a grinding agent such as silicon carbide, and said microorganism is thus introduced into the leaves and stems of the plant. The methods (b) for the coating of the seeds include, for example, the coating of the seed surface with a suspension containing the microorganisms mentioned above and methyl cellulose (or gum arabic), and the drying of the seeds. The methods (c) for the mixture with the soil include, for example, the mixture of the above microorganism with the soil before the plant is permanently planted, or the scattering method. With any method mentioned above, the microorganism that can decompose or detoxify fusaric acid can be used in cell form, as a cell homogenate, and/or as a cell extract.

By the above-mentioned methods, the plant diseases caused by species of Fusarium can be effectively prevented by the decomposition or detoxification for plants of the fusaric acid produced by the species of Fusarium.

EXAMPLE 1—1

To BMM medium with the following composition, fusaric acid was added at the concentration of 100 µg/ml as the sole carbon source, resulting in the desired culture medium.

| BMM Medium | |
|---|---|
| $(NH_4)_2SO_4$ | 2 g |
| $NaH_2PO_4 \cdot H_2O$ | 0.5 g |
| $K_2HPO_4$ | 0.5 g |
| $MgSO_4 \cdot 7H_2O$ | 0.2 g |
| $CaCl_2$ | 0.1 g |

| BMM Medium -continued | |
|---|---|
| Water | 1000 ml |

*Cladosporium werneckii* DK2011 was cultured on this medium at 30° C. for five days with agitation. The culture fluid was centrifuged, resulting in a supernatant, the absorbance ($A_s$) at 270 nm of which was measured. Separately, medium was agitated under the same conditions without a bacterial inoculation as the control medium, the medium was centrifuged, resulting in a supernatant; and the absorbance ($A_c$) of the supernatant was measured. The activity of both preparations to decompose fusaric acid was then calculated by the following formula:

$$\text{Activity for decomposition of fusaric acid (units)} = \frac{A_c - A_s}{\text{Culture time (hr)}} \times 1000$$

The results are shown in Table 4. The amount of fusaric acid remaining was calculated from the absorbance at 270 nm ($OD_{270}$).

TABLE 4

| *Cladosporium werneckii* | Decomposition activity (units) | Fusaric acid remaining (μg/ml) |
|---|---|---|
| DK2011 | 32 | 0.8 |
| Control | 0 | 100 |

EXAMPLE 1-2

Tomato cuttings were left at room temperature in the supernatant of the culture fluid obtained in Example 1—1. The cuttings were inspected by the naked eye one week later, and changes were not seen.

When tomato cuttings were left at room temperature in the control medium of Example 1—1, chlorosis occurred along the veins of the leaves, and the cuttings had withered and died within one week.

EXAMPLE 1-3

The strain used in Example 1—1 was cultured in a medium that was prepared by the addition of 20 mg/ml glucose and 100 μg/ml fusaric acid to BMM medium. The resultant cells were collected by the ordinary methods such as centrifugation, etc. These cells were added to the concentration of 5% (wet weight) to a phosphate buffer(pH 7.0) that contained fusaric acid at the concentration of 100 μg/ml. This mixture was agitated for 24 hours at 30° C. The concentration of fusaric acid that remained in the buffer was 20 μg/ml.

EXAMPLE 1-4

The same strain of microorganism as was used in Example 1—1 was cultured in the same medium as in Example 1-3. The cells were disrupted by the use of an ultrasonic oscillator, and the resultant cell homogenate was added to the concentration of 5% (wet weight) to the same buffer containing fusaric acid as in Example 1-3. The mixture was agitated for 12 hours at 30° C. All of the fusaric acid was found to have been decomposed.

EXAMPLE 2-1

Soil obtained in the Kowakae area of Higashi-Osaka City, Japan, was suspended in sterilized water, and the supernatant obtained was diluted, spread onto the screening medium described in Table 5, in which the sole carbon source was fusaric acid, and then cultured for 48 hours at 30° C.

TABLE 5

| $K_2HPO_4$ | 7 g |
|---|---|
| $KH_2PO_4$ | 2 g |
| $MgSO_4$ | 0.1 g |
| $(NH_4)_2SO_4$ | 1 g |
| Fusaric acid | 100 mg |
| Agar | 15 g |
| Water | 1 l |

The colonies that were produced were inoculated again onto the same medium, and the resultant species were identified by their bacteriological characteristics shown in Table 1. This strain was named *Pseudomonas cepacia* UK-1.

This *Pseudomonas cepacia* UK-1 was cultured in the medium described in Table 5 (liquid medium without agar) at 30° C. for three days with agitation. The culture fluid was centrifuged, and the supernatant collected. Its absorbance at 270 nm was measured. Separately, medium was agitated under the same conditions without a bacterial inoculation as the control medium, the culture fluid centrifuged, and the resultant supernatant measured for absorbance. Then the activity of the two preparations to decompose fusaric acid was calculated. The fusaric acid concentration of the control medium was 100 μg/ml, and that of the culture fluid of this strain was 0.3 μg/ml.

EXAMPLE 2—2

To the medium described in Table 5 (liquid medium without agar), glucose was added to the concentration of 2 g/l. On the resultant medium, *Pseudomonas cepacia* UK-1 was cultured, its culture fluid centrifuged, and the resultant supernatant collected. This supernatant was mixed with a solution of physiological saline that contained fusaric acid at the concentration of 100 μg/ml so that the culture fluid reached the concentration of 5% (wet weight), and this mixture was agitated at 30° C. for 24 hours. The amount of fusaric acid that remained in the liquid was 7 μg/ml.

EXAMPLE 2-3

A suspension of *Pseudomonas cepacia* UK-1 was made with cells at the concentration of $10^9$/ml in pure water. Pure water was used as the control. Two groups of tomatoes in the fifth to sixth internodal growth period, each group containing five tomato cuttings, were used. The cut ends of the tomatoes were submerged for 3 hours in the suspension mentioned above and water for the test and the control groups, respectively. Then the cut ends were washed with water, and put in about 20 ml of an aqueous solution of fusaric acid at the concentration of 300 μg/ml. They were left until 10 ml of the solution had been absorbed. Then the cut ends were washed with water and said ends were put in water and left at 20° C.

When the water control was used, symptoms of withering of all of the leaves were seen 8 to 16 hours after the beginning of the soaking in the aqueous solution of fusaric acid, and the stems and veins of the leaves turned brown and died. When the suspension of the UK-1 strain was used, no symptoms were found in any of the five cuttings 72 hours later.

EXAMPLE 2-4

*Pseudomonas cepacia* UK-1 was cultured in the medium described in Table 5 (liquid medium without agar). A portion of the culture fluid was taken at the start of culture and 24, 48, and 72 hours after. Each portion was centrifuged at 3000×g to obtain a supernatant, which was filtered with the use of a membrane filter with 0.2- μm pores. The filtrate obtained and Murashige-Skoog (MS) medium (Physiol. Planta 15, 473 (1962)) were mixed at the ratio of 1:9. Then callus induced from the cambium of tomato (*Lycopersicon esculentum* Mill cv. Zuiko) was added to the mixture to the concentration of $10^4$–$10^5$ cells per milliliter of medium and left for 24 hours at 25° C. Then the callus cells were stained with fluorescein diacetate (FDA). The stained cells were observed under a fluorescence microscope, and the percentage of callus cells that had survived was calculated (n=500). As a control, MS medium was used instead of the mixture mentioned above. The results are shown in Table 6.

TABLE 6

| | Surviving tomato callus cells (%) |
|---|---|
| At start | 0.4 |
| 24 hr later | 48.9 |
| 48 hr later | 66.9 |
| 72 hr later | 86.2 |
| Control | 87.0 |

EXAMPLE 3-1

A strain of *Pseudomonas solanacearum*, TU-10, was isolated from tobacco plants infected with damping-off (identified by reference to Bergey's Manual of Systematic Bacteriology, vol. 1).

From this strain Pseudomonas solanacearum TU-10, a non-pathogenic strain, TU-10A, was isolated by the usual methods. This strain TU-10A was treated with NTG by the method of Adelberg et al., and inoculated on a PCG medium that contained 100 ppm of fusaric acid. The strain that grew best on this medium was selected. This strain was named *Pseudomonas solanacearum* N50A16. The strain was cultured for 3 days with agitation at 30° C. on the medium described in Table 7.

TABLE 7

| Composition of medium | | |
|---|---|---|
| Inorganic salts | $Na_2HPO_4$ | 7 g |
| | $KH_2PO_4$ | 3 g |
| | NaCl | 0.5 g |
| | $NH_4Cl$ | 1 g |
| | $CaCl_2$ | 0.1 g |
| | $MgSO_4$ | 1 g |
| Casamino acids | | 4 g |
| Fusaric acid | | 100 mg |
| Water (pH of medium, 6.5) | | 1 l |

The culture fluid was centrifuged at 3000×g for 10 minutes to collect a supernatant, which was filtered through a membrane filter with 0.2 μm pores. The filtrate obtained and Murashige-Skoog (MS) medium (Physiol. Planta 15, 473 (1962)) were mixed at the ratio of 1:9, resulting in a culture fluid (culture fluid 1). Then callus induced from the cambium of stalk of tomato (*Lycopersicon esculentum* Mill cv. Zuiko) was added to the mixture to the concentration of $10^4$–$10^5$ cells per milliliter of medium and left for 24 hours at 25° C. The callus cells were stained with fluorescein diacetate (FDA). The stained cells were observed under a fluorescence microscope and the percentage of cells that had survived was calculated (n=500). As a control, MS medium was used instead of culture fluid 1. At this time, the value was 100%. Separately, the same experiment was carried out with tomato callus cells except that the medium described in Table 7 without the fusaric acid was mixed with MS medium in a 1:9 ratio (culture fluid 2).

Moreover, a mixture was made of the medium described in Table 7 and MS medium in the ratio of 1:9 (culture fluid 3; the concentration of fusaric acid was about 10 ppm) and the same kind of experiment was done as described above with tomato callus cells. The percentage of surviving cells was calculated, and the results are shown in Table 8.

TABLE 8

| | Medium composition | Surviving tomato callus cells (%) |
|---|---|---|
| Control | MS medium | 100 |
| Culture fluid 1 | Filtrate of culture fluid (obtained using minimal medium + casamino acids + fusaric acid) + MS medium | 64.3 |
| Culture fluid 2 | (Minimal medium + casamino acids) + MS medium | 99.7 |
| Culture fluid 3 | (Minimal medium + fusaric acid + casamino acids) + MS medium | 9.2 |

Table 8 shows that when tomato callus cells are added to culture fluid 3 containing fusaric acid, more than 90% of tomato callus cells have died in 24 hours, but that more than 60% of the cells survive in culture fluid 1 containing N50A16 culture fluid.

EXAMPLE 3-2

The non-pathogenic strain of *Pseudomonas solanacearum* TU-10A and the *Pseudomonas solanacearum* N50A16 obtained in Example 3-1 were added to 10 ml of pure water, each at the concentration of $10^9$ cells/ml, and suspended. Five cuttings of tomato in the fifth to sixth internodal growth period were used in the test. Their cut ends were submerged for 3 hours in the suspension mentioned above or in pure water. Then the cut ends were washed with water and put in about 20 ml of an aqueous solution of fusaric acid at the concentration of 300 μg/ml. They were left until 10 ml of the solution had been absorbed. Then the cut ends were washed with water and said ends were put in water and left at 20° C.

When the water control or the non-pathogenic strain TU-10A was absorbed, all of the leaves of the cuttings showed symptoms of withering 8 to 16 hours after the beginning of the soaking in the aqueous solution of fusaric acid, and the stems and veins of the leaves turned brown and died. However, when the suspension of the N50A16 strain was used, no symptoms were found in any of the five cuttings even 72 hours later.

EXAMPLE 4-1

(A) DNA preparation: *Cladosporium werneckii* DK2011 was cultured for three days in 2 liters of peptone-yeast extract medium (PYE; 0.3% peptone, 0.3% yeast extract) at 30° C. in Erlenmeyer flasks. The culture fluid was centrifuged, and the cells in the precipitate were suspended in 100 mM EDTA, pH 8.5. This suspension was frozen at −80° C., and then allowed to thaw at 30° C. These procedures were repeated three times. The cells were ground fine with a homogenizer, and centrifuged at 10000×g for 15 minutes. To the resultant precipitate, a solution (pH 7.8) containing 0.2% SDS, 50 mM Tris-HCl, 100 mM EDTA, and 50 mM NaCl was added at the concentration of 2 g of the above-mentioned cells (wet weight) per 10 ml of solution. This mixture was incubated for 15 minutes at 68° C. and centrifuged at 10000×g for 15 minutes. To the resultant supernatant, RNase A (Sigma) that had been heated for 15 minutes at 100° C. to remove DNase activity was added to the final concentration of 100 μg/ml. This mixture was incubated for 20 minutes at 30° C., and then proteinase K (Boehringer) was added to the final concentration of 50 μg/ml. This mixture was incubated for 20 minutes at 37° C., and treated with phenol twice. Then, to the water phase, an equal volume of a 24:1 mixture of chloroform and isoamyl alcohol was added, and the resultant mixture was centrifuged at 8000×g for 10 minutes. Then, to the resultant supernatant, one-tenth volumes of 3 M sodium acetate and three volumes of cold ethanol were added. This mixture was kept at −70° C. for 20 minutes to allow the DNA to precipitate. The mixture was then centrifuged at 10000×g for 15 minutes and the ethanol was removed from the precipitated DNA by being dried. The precipitate was dissolved in sterilized water to the final concentration of 0.5 μg/ml. In this way, fluid that contained about 1 mg of DNA was obtained. This DNA was found by electrophoresis to have been cleaved during the procedures described above.

(B) CLONING

(B)-1 Cleavage of pNO1523 at the SmaI position

As the vector, pNO1523 (Pharmacia) was used; this was a vector in which the gene for streptomycin sensitivity was introduced into pBR322 (Dern, Gene, 15, 99–102 (1981)). A mixture of 40 μl of pNO1523 (0.3 μg/μl), 2 μl of SmaI (5 units/μl; Nippon Gene), 5 μl of ×10 reaction mixture for SmaI, and 3 μl of sterilized water was incubated at 30° C. for 1 hour, treated with phenol, and precipitated with ethanol. The precipitate was dissolved in 40 μl of Tris-EDTA (TE) buffer. A 10-μl portion of this solution was treated by electrophoresis, and the results showed that the pNO1523 had been cleaved at the SmaI site.

(B)-2 Ligation

A mixture was made of 5 μl of the solution containing pNO1523 cleaved at the SmaI site obtained in this way, 3 μl of the DNA solution (5 μg/μl) obtained as described in section A, 1 μl of T4 ligase (300 units/μl), 2 μl of ×10 reaction mixture for T4 ligase (which contained 500 mM Tris-HCl, pH 7.9, 100 mM MgCl2, and 200 mM ditiothreitol), 2 μl of 10 mM ATP, and 7 μl of sterilized water. This mixture was allowed to react at 16° C. overnight.

(C) Transformation

The reaction mixture obtained in Section B was brought into contact with E. coli HB101 cells that had been treated with CaCl2, resulting in recombinants, which were then applied to L broth agar medium containing streptomycin (100 μg/ml) and ampicillin (50 μg/ml), and cultured at 37° C. for 24 hours. The details of the CaCl2 treatment of the bacteria and of the recombination techniques were as described by Ikeda et al. (Lectures in Genetic Experimentation, vol. 1, p. 131 (1983) published by Kyoritsu Shuppan; eds., H. Ozeki, R. Shimura).

(D) Screening for the gene controlling detoxification of fusaric acid

About 500 cells of the bacteria obtained in Section C were replicated on agar medium of L broth that contained fusaric acid at the concentration of 50 μg/ml, and strains that were resistant to fusaric acid were selected. Recombinants that were resistant to fusaric acid were obtained. Of them, a recombinant that had the greatest resistance was selected. This was cultured, and the plasmids from these cells were obtained by the alkaline-SDS method. The plasmids were once more introduced into E. coli HB101 cells, and it was found that the recombinant strain had a high ability to detoxify fusaric acid. This plasmid of E. coli was named pFS4, and the above-mentioned recombinant into which pFS4 had been introduced was named *Escherichia coli* pFS4/HB101 (FERM BP-1386). This recombinant had the same bacteriological characteristics as its parent strain with the exception of its ability to detoxify fusaric acid.

EXAMPLE 4–2

The recombinant obtained in Section D, E. coli pFS4/HB101, was cultured on L broth medium at 37° C., and the resultant cells were suspended in physiological saline to the concentration of $10^9$ cells/ml. Separately, E. coli HB101 into which only the vector plasmid pNO1523 had been introduced, called strain pNO1523/HB101, was produced by the methods described in Example 4–1. In the same way as before, a cell suspension of $10^9$ cells per milliliter of physiological saline was prepared. Then five cuttings of tomato in the fifth to sixth internodal growth period were used in the following tests. Their cut ends were submerged for 3 hours in the suspension mentioned above or in physiological saline. Then the cut ends were washed with water and put in about 15 ml of an aqueous solution of fusaric acid of the concentration of 100 μg/ml. They were left for 40 hours to absorb the solution. The volume of fusaric acid solution that had been absorbed or that had evaporated was replaced with water to maintain the total volume of the fusaric acid solution at the value of about 15 ml.

When the saline control or the suspension of pNO1523/HB101 was used, the stalks, first, withered and died. However, when the suspension of the strain pFS4/HB101 was used, no abnormalities were found in any of the five cuttings.

EXAMPLE 4–3

The strain pFS4/HB101 obtained in Example 4–1 was inoculated on L broth medium that contained fusaric acid at the concentration of 50 μg/ml and cultured at 30° C. with agitation. A portion was sampled at the start of culture and at 24, 28, and 72 hr after. These samples were centrifuged to obtain their supernatants.

These supernatants were filtered through a membrane filter with 0.2-μm pores. The filtrate obtained was mixed with Murashige-Skoog (MS) medium (Physiol. Planta 15, 473 (1962), in a 1:4 ratio. Then, to the mixture, callus induced from the cambium of stalks of tomato (*Lycopersicon esculentum* Mill cv. Zuiko) was added to the concentration of $10^4$–$10^5$ cells/milliliter of medium and left for 24 hours at 25° C. Then the cells were stained with fluorescein diacetate (FDA). The stained cells were observed under a fluorescence microscope and the percentage of cells that had survived was calculated (n=500). The percentage of surviving tomato callus cells is shown in Table 9.

TABLE 9

| | Surviving tomato callus cells (%) |
|---|---|
| At start | 6.9 |
| 24 hr later | 19.4 |
| 48 hr later | 40.4 |
| 72 hr later | 51.3 |
| Control | 87.0 |

EXAMPLE 5-1

Tomatoes were grown in vermiculite of a pot for about 30 days after being sown until they were in the fourth internodal growth period. Then a razor blade was inserted 5 cm deep into the vermiculite at a point 2 cm from the base of the tomato stalk, and used to cut along a line 5 cm long and 5 cm deep, so as to cut the tomato roots in the vicinity. To the portions, 10 ml of a suspension of *Pseudomonas solanacearum* N50A16 suspended in physiological saline at the concentration of $10^7$ cells/ml was applied (injured root inoculation method). For comparison, instead of the suspension mentioned above, 10 ml of water or 10 ml of a suspension of the non-pathogenic strain *Pseudomonas solanacearum* TU-10A at the concentration of $10^7$ cells/ml was used in the same way. The wounds in the roots were allowed to heal during another one week of growth. The vermiculite was removed and the roots were washed with water. Then the roots were dipped in 50 ml of a suspension of the spores of *Fusarium oxysporum* f. sp. lycopersici ($10^7$ spores/ml) for several minutes (root-immersion inoculation method). The roots were then transplanted without being washed with water to fresh vermiculite and grown at 20° C. Separately, without an introduction of the suspension of the strain N50A16, and without being dipped in the above suspension of Fusarium spores, tomato plants were grown in the same way.

With the tomato plants into which the strain N50A16 as introduced, no abnormalities were found during the experimental periods for 2 months, and the extent of growth was about the same as that of the tomato plants non-inoculated with the Fusarium spores. With the tomato plants treated with water or the strain TU-10A, however, the leaves showed symptoms of blight 8 days after inoculation with Fusarium. One month after having been infected, their growth was strongly inhibited, the lower leaves had withered, and the were few and their growth was not vigorous.

EXAMPLE 5-2

Instead of *Pseudomonas solanacearum* N50A16, *Cladosporium werneckii* DK2011 was used in the same experiment as in Example 5-1, except that water only was used as the control. The same results as in Example 5-1 were obtained.

EXAMPLE 5-3

Instead of *Pseudomonas solanacearum* N50A16, *Pseudomonas cepacia* UK-1 was used in the same experiment as in Example 5-1, except that water only was used as the control. The same results as in Example 5-1 were obtained.

EXAMPLE 5-4

The same experiment as in Example 5-1 was carried out except that first, *E. coli* pFS4/HB101 was used instead of *Pseudomonas solanacearum* N50A16 and second, water or *E. coli* pNO1523/HB101 was used for comparison. The same results as for Example 5-1 were obtained. The strain pNO1523/HB101 is a strain that was obtained by the introduction of the vector pNO1523 alone into the host organism by the same procedures as in the above-mentioned strain pFS4/HB101.

EXAMPLE 5—5

The stalk of tomatoes was cut and submerged in 10 ml of a suspension of *Pseudomonas solanacearum* N50A16 at the concentration of $10^7$ cells/ml for three hours. The cut ends were washed with water and left in water at room temperature. Then, after adventitious roots were developed, the roots were dipped in 50 ml of a suspension of *Fusarium oxysporum* f. sp. lycopersici spores at the concentration of $10^7$ spores/ml. Without being washed with water, the tomatoes were planted in filled with fresh vermiculite, and grown at 20° C. For comparison, instead of the suspension of the strain N50A16 mentioned above, water or a suspension of the non-pathogenic *Pseudomonas solanacearum* TU-10A was used, with other procedures unchanged. Separately, without being submerged in the suspension of the strain N50A16, and without being dipped in the Fusarium suspension, tomato plants were grown in the same way.

Two months after the strain N50A16 was introduced into tomato plants, no abnormalities were found, and the extent of growth was about the same as that of the tomatoes non-inoculated with Fusarium. However, in the tomato plants that were treated with water or with the strain TU-10A, leaf withering appeared 8 days after inoculation with the Fusarium spores. One month after the infection, the inhibition of growth was marked, with extensive withering of the lower leaves and browning of the stalk. The numbers of stalk nodes were few and their growth was not vigorous.

EXAMPLE 5-6

The same experiment as in Example 5—5 was carried out except that first, *Cladosporium werneckii* DK2011 was used instead of *Pseudomonas solanacearum* N50A16 and second, water only was used as the control. The same results as for Example 5—5 were obtained.

EXAMPLE 5-7

The same experiment as in Example 5—5 was carried out except that first, *Pseudomonas cepacia* UK-1 was used instead of *Pseudomonas solanacearum* N50A16 and second, water only was used as the control. The same results as for Example 5—5 were obtained.

EXAMPLE 5-8

The same experiment as in Example 5—5 was carried out except that first, *E. coli* pFS4/HB101 was used instead of *Pseudomonas solanacearum* N50A16 and second, water or *E. coli* pNO1523/HB101 was used as the control. The same results as for Example 5—5 were obtained.

EXAMPLE 5-9

The same experiment as in Example 5-1 was carried out except that first, strawberries were used instead of tomatoes and second, *Fusarium oxysporum* f. sp. fragariae was used instead of *Fusarium oxysporum* f. sp. lycopersici. The same results as for Example 5-1 were obtained.

EXAMPLE 5-10

The same experiment as in Example 5-9 was carried out except that *Cladosporium werneckii* DK2011 was used instead of *Pseudomonas solanacearum* N50A16. The same results as for Example 5-9 were obtained.

EXAMPLE 5-11

The same experiment as in Example 5-9 was carried out except that *Pseudomonas cepacia* UK-1 was used instead of *Pseudomonas solanacearum* N50A16. The same results as for Example 5-9 were obtained.

EXAMPLE 5-12

The same experiment as in Example 5-9 was carried out except that *E. coli* pFS4/HB101 or *E. coli* pNO1523/HB101 were used instead of *Pseudomonas solanacearum* N50A16. The same results as for Example 5-9 were obtained.

EXAMPLE 5-13

Field soil (4000 ml) was sterilized and mixed L with a suspension in water of cells of *Pseudomonas solanacearum* N50A16 (100 ml; $10^7$ cells/ml). Separately, the same amount (4000 ml) as mentioned above of field soil was sterilized and mixed with 100 ml of a suspension of the spores of *Fusarium oxysporum* f. sp. lycopersici at the concentration of $10^7$ spores/ml. These samples of field soil containing these bacterial suspensions were mixed to uniformity, and put into 1/5000 R Wagner pots. For comparison, instead of the above-mentioned strain N50A16, the non-pathogenic strain *Pseudomonas solanacearum* TU-10A was used. Tomato seedlings about 20 days old were planted into the pots, and grown at 20° C. for 2 months. The seedlings in the pot that contained the mixture of soil with the strain N50A16 mentioned above grew normally, but the tomato seedlings in the pot that contained soil mixed with the strain TU-10A were markedly inhibited in their growth.

EXAMPLE 5-14

The same experiment as in Example 5-13 was carried out except that first, *Cladosporium werneckii* DK2011 was used instead of *Pseudomonas solanacearum* N50A16 and second, water was used instead of the suspension of cells of the non-pathogenic strain *Pseudomonas solanacearum* TU-10A. The same results as for Example 5-13 were obtained.

EXAMPLE 5-15

The same experiment as in Example 5-13 was carried out except that first, *Pseudomonas cepacia* UK-1 was used instead of *Pseudomonas solanacearum* N50A16 and second, water was used instead of the suspension of cells of the non-pathogenic strain *Pseudomonas solanacearum* TU-10A. The same results as for Example 5-13 were obtained.

EXAMPLE 5-16

Tomato seeds, *Pseudomonas solanacearum* NO50A16, gum arabic, and water were mixed with a concentration of the *Pseudomonas solanacearum* N50A16 at $10^8$ cells/ml, and that of the gum arabic 30%, resulting in a colloid-like mixture. This colloid mixture had about 1 seed/0.1 g. The mixture was dried at 30° C. for 20 hours so as to produce coated seeds. For comparison, instead of the strain N50A16, the nonpathogenic *Pseudomonas solanacearum* TU-10A was used in the coating of the seeds. These seeds were sown in a pot filled with vermiculite and grown at 20° C. for 30 days. The tomato seedlings obtained were pulled up, and their roots were dipped for several minutes in 50 ml of a spore suspension of *Fusarium oxysporum* f. sp. lycopersici at the concentration of $10^7$ spores/ml. These tomato seedlings were transplanted to a pot filled with fresh vermiculite, and grown for 2 more months at 20° C. The tomato plants obtained from seeds coated with the strain N50A16 mentioned above grew normally, but the tomato plants grown from seeds coated with the strain TU-10A mentioned above were markedly inhibited in their growth.

EXAMPLE 5-17

The same experiment as in Example 5-16 was carried out except that first, *Cladosporium werneckii* DK2011 was used instead of *Pseudomona solanacearum* N50A16 and second, the non-pathogenic strain *Pseudomonas solanacearum* TU-10A was not used. The same results as for Example 5-16 were obtained.

EXAMPLE 5-18

The same experiment as in Example 5-16 was carried out except that first, *Pseudomonas cepacia* UK-1 was used instead of *Pseudomonas solanacearum* N50A16 and second, the non-pathogenic strain *Pseudomonas solanacearum* TU-10A was not used. The same results as for Example 5-16 were obtained.

It is understood that various other modifications will be apparent to and can be readily made by those skilled in the art without departing from the scope and spirit of this invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art to which this invention pertains.

What is claimed is:

1. A method for the prevention of Fusarium diseases in a plant, comprising:
   applying a microorganism capable of decomposing fusaric acid to said plant or to the soil around said plant, wherein said microorganism is *Cladosporium werneckii* DK2011 (FERM BP-1383).

2. A method for the prevention of Fusarium diseases in a plant, comprising:
   applying a microorganism capable of detoxifying fusaric acid to said plant or to the soil around said plant, wherein said microorganism is *Pseudomonas solanacearum* N50A16 (FERM BP-1384).

3. A method for the prevention of Fusarium diseases in a plant, comprising:
   applying a microorganism capable of detoxifying fusaric acid to said plant or to the soil around said plant, wherein said microorganism is *E. coli* pFS4/HB101 (FERM BP-1386).

4. A biologically pure culture of microorganism having the ability to decompose fusaric acid, wherein said microorganism is *Cladosporium werneckii* DK2011 (FERM BP-1383).

5. A biologically pure culture of microorganism having the ability to detoxify fusaric acid for plants, wherein said microorganism is *Pseudomonas solanacearum* N50A16 (FERM BP-1384).

6. A biologically pure culture of microorganism having the ability to detoxify fusaric acid for plants, wherein said microorganism is *E. coli* pFS4/HB101 (FERM BP-1386).

* * * * *